(12) United States Patent
Gatto

(10) Patent No.: US 6,846,311 B2
(45) Date of Patent: Jan. 25, 2005

(54) METHOD AND APPARATUS FOR IN VIVO TREATMENT OF MAMMARY DUCTS BY LIGHT INDUCED FLUORESCENCE

(75) Inventor: Dominick L. Gatto, Branford, CT (US)

(73) Assignee: Acueity, Inc., Palo Alto, CA (US)

( * ) Notice: Subject to any disclaimer, the term of this patent is extended or adjusted under 35 U.S.C. 154(b) by 161 days.

(21) Appl. No.: 10/212,280

(22) Filed: Aug. 6, 2002

(65) Prior Publication Data

US 2003/0187427 A1 Oct. 2, 2003

Related U.S. Application Data

(63) Continuation-in-part of application No. 10/112,954, filed on Apr. 2, 2002.

(51) Int. Cl.[7] ............................................. A61B 18/18
(52) U.S. Cl. .............................. 606/15; 606/3; 606/14; 607/88; 607/89; 128/898; 600/101; 600/160
(58) Field of Search ................................. 606/3, 13–16; 607/88, 89; 128/898; 600/101, 156, 160, 563–566; 604/19, 20, 28, 35, 500–502

(56) References Cited

U.S. PATENT DOCUMENTS

| | | |
|---|---|---|
| 4,556,057 A | 12/1985 | Hiruma et al. |
| 5,087,636 A | 2/1992 | Jamieson et al. |
| 5,095,030 A | 3/1992 | Levy et al. |
| 5,149,708 A | 9/1992 | Dolphin et al. |
| 5,211,938 A | 5/1993 | Kennedy et al. |
| 5,214,036 A * | 5/1993 | Allison et al. ............... 514/185 |
| 5,258,453 A | 11/1993 | Kopecek et al. |
| 5,283,225 A | 2/1994 | Neumann et al. |
| 5,308,608 A | 5/1994 | Dolphin et al. |
| 5,314,905 A | 5/1994 | Pandey et al. |
| 5,418,169 A | 5/1995 | Crissman et al. |
| 5,556,764 A | 9/1996 | Sizto et al. |
| 5,605,805 A | 2/1997 | Verwer et al. |
| 5,627,040 A | 5/1997 | Bierre et al. |
| 6,221,622 B1 | 4/2001 | Love |
| 6,500,114 B1 * | 12/2002 | Petitto et al. ............... 600/156 |
| 6,652,442 B2 * | 11/2003 | Gatto ............................ 600/3 |

* cited by examiner

*Primary Examiner*—A. Farah
(74) *Attorney, Agent, or Firm*—Olson & Hierl, Ltd.

(57) ABSTRACT

The invention is directed toward a micro-endoscope assembly for the treatment of diseased tissue in breast ducts comprising a cylindrical guide tube with a distal end defining an internal cylindrical passageway, a first smaller cylindrical tube eccentrically formed in the cylindrical passageway of a smaller diameter than said tube internal cylindrical passageway to receive and guide an endoscope, the smaller cylindrical tube forming together with an inner wall surface of the cylindrical guide tube a second passageway. A light transmitting probe is mounted in the second passageway and is connected at the distal end of the guide tube with an energy transmitting device. The light probe is activated to generate light at a particular wavelength to cause the tissue to fluoresce and is again activated to generate light at a specific wavelength to necrose the diseased tissue.

21 Claims, 2 Drawing Sheets

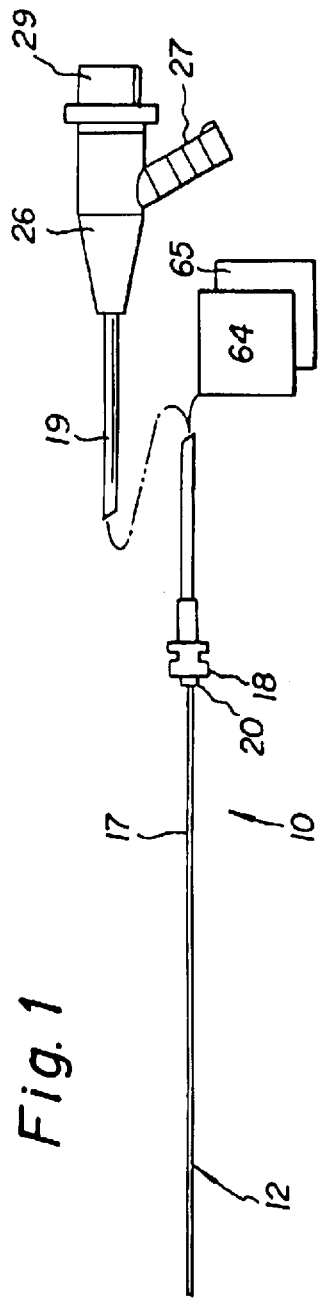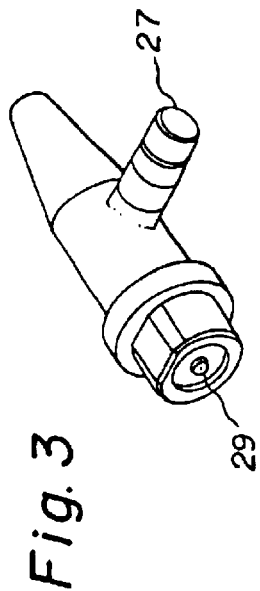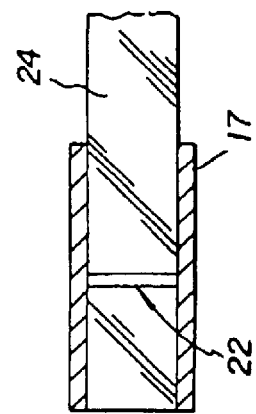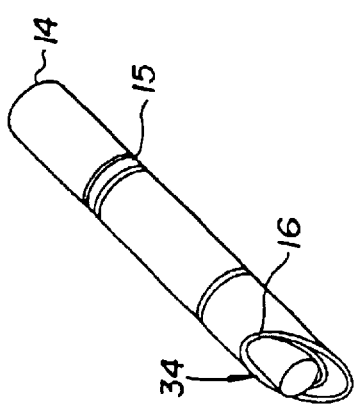

METHOD AND APPARATUS FOR IN VIVO TREATMENT OF MAMMARY DUCTS BY LIGHT INDUCED FLUORESCENCE

RELATED APPLICATION

This is a continuation-in-part application of U.S. patent application Ser. No. 10/112,954 filed Apr. 2, 2002 entitled Apparatus and Method for Intraductal Abalation by the same inventor as this application.

FIELD OF INVENTION

The present invention is generally directed toward the treatment of breast cancer and more specifically toward the treatment of atypical tissue and cells in the mammary breast ducts of women by detecting atypical tissue by administering a compound which is converted into a photosensitizer by the diseased or atypical cells in the mammary duct transmitting a light of predetermined wave length to be absorbed by the sensitizer which can be directly viewed to locate the diseased atypical cells, and further treated with additional light to kill the atypical cells.

BACKGROUND OF THE INVENTION

A leading disease incurred by women is breast cancer. Breast cancer is the second leading cause of death for women of all ages and the leading cause of death for women aged 25–55. Approximately one in eight women will incur breast cancer in their lifetimes. Approximately 220,000 surgeries are performed annually in the United States with almost 20 percent requiring the complete removal of the breast.

The current medical standard for determining breast cancer in women is mammography. For breast cancer detection, other than clinical examination and self-examination, women rely almost exclusively on mammography. It is estimated that more than 30 million mammograms are performed each year in the U.S. alone. Mammography is so insensitive that typically the average size of the tumor which can be detected is approximately 1.5 cm At that size, a tumor has probably been growing, undetected, for nearly 8 years on average. In fact, two-thirds of mammographically detected breast cancer is invasive. In addition, mammography is notorious for "false positive" readings, which lead to many unneeded biopsies. However mammography fails to detect up to 20% of breast cancers in women over 50 and up to 40% of breast cancers in younger women. Medical researchers have long recognized that nearly all breast cancer originates in the epithelial lining of the mammary duct system. Furthermore, it is well established that, in its early stages, most breast cancer develops very slowly and remains confined to the mammary ducts for up to 7–10 years. If these very early stages of premalignant and malignant disease could be detected and treated while within the mammary duct system, the result would be substantially better treatment outcomes: enhanced survivability, avoidance of chemotherapy and radiation, and breast conservation.

After detection breast cancer is generally treatable in three ways: surgery, radiation and chemotherapy. Surgery and radiation, of course, have risks and disadvantages well known to those skilled in the art. Chemotherapy may be disadvantageous as when the drugs involved cause sickness to the patient when they enter the blood stream.

Today's primary treatment of breast cancer is traditional surgery, either mastectomy or lumpectomy with radiation therapy. Surgery is, by definition, invasive and traumatic. Because the exact margins of cancerous growth are difficult to pinpoint, a surgeon may remove more breast tissue than is necessary or not remove enough. Between newly diagnosed breast cancer surgeries and re-excisions, approximately 180,000 lumpectomies are performed each year in the United States.

Mammary Intraductal Treatment (MIT) refers to a procedure in which abnormal cells in the lining of the mammary duct are destroyed to control abnormal intraductal pathology that may or may not be related to malignancy. Today, women with positive mammograms, positive biopsies or intraductal atypical (abnormal pathology) often have a choice of watchful waiting, medical therapy, or surgery (lumpectomy and mastectomy). The advancement of new technology and techniques for the treatment of breast disease has not kept pace with other medical areas, particularly in the area of minimally invasive techniques (mammary ductoscopy).

Benign conditions that can lead to abnormal intraductal assessment include intraductal papilloma, hyperplasia and atypical ductal hyperplasia and these can be removed without requiring invasive surgery. Likewise, hormonal therapies, and pharmaceutical agents (Tamoxifen) may control the growth of intraductal cancerous lesions. Intraductal treatment can be indicated for women who have not responded to medical therapy or choose not to take the agents due to side effects or other personal reasons. All women should have biopsies or intraductal samplings (lavage) to confirm the presence of atypical or malignant disease.

The present detection technique utilizes the mammary ductoscope allowing the physician to look directly into the mammary ducts to determine tissue fluorescense.

Attempts have been made to provide an instrument which will allow the taking of tissue samples within small duct areas. A simple double barrel catheter with adjacent lumens is disclosed in U.S. Pat. No. 6,221,622 with one of the lumens being used to irrigate the milk duct of a breast and the other lumen being used to aspirate the fluid which has entered the duct allowing a continuous flow of saline through the duct which hopefully carries enough cells and tissues for a biopsy. Problems in the use of such an instrument include the small size required by the narrow small diameter lumens which can be blocked or limit the flow of fluid back through the aspiration lumen and thus preclude significant tissue collection or cause duct collapse. While the '622 Patent shows a small lumen size, the size problem is magnified when the other existing prior art is attempted to be applied to breast ducts because of the small size and thin cell walls of the mammary ducts which can be ruptured.

Fluorescent substances in an organism are exemplified by NADH (nicotinamide adenine nucleotide), FMN (flavin mononucleotide) and pyridine nucleotide. The relationship between the intrinsic substances in an organism and the diseases has been clarified. If textures of an organism are irradiated with excitation light, fluorescent light having a wavelength longer than that of the excitation light is generated. Each of HpD (Hematoporphyrin), Photofrin and ALA (beta-aminolevulminic acid) has integrating characteristics into a cancer. By injecting any of the foregoing substances into an organism, irradiating the subject portion with excitation light and observing fluorescent light, a disease portion can be diagnosed and treated.

U.S. Pat. No. 4,556,057 discloses a system comprising a diagnosing laser beam source, a curing laser beam source and a normal photographing light source. The normal photographing light source is controlled in synchronization with the activation/deactivation of the diagnosing light source and fluorescent light generated due to irradiation with excitation light is captured by an image sensing apparatus having an image intensifier by a normal image sensing apparatus. The observed fluorescent image and observed normal image are displayed on monitors which correspond to the image sensing apparatuses so that a cancer can be diagnosed and cured.

I. Photodynamic Therapy

The destruction of the intraductal epithelial tissue can be performed by various energy delivering devices, namely, fluorescence.

It has been known for many years that photosensitizing compounds show a photochemical reaction when exposed to light. Photodynamic therapy (PDT) uses such photosensitizing compounds and lasers to produce tumor necrosis. Treatment of solid tumors by PDT usually involves the systemic administration of tumor localizing photosensitizing compounds and their subsequent activation by laser. Upon absorbing light of the appropriate wavelength the sensitizer is converted from a stable atomic structure to an excited state. Cytotoxicity and eventual tumor destruction are mediated by the interaction between the sensitizer and molecular oxygen within the treated tissue to generate cytotoxic singlet oxygen.

Two good general references pertaining to PDT, biomedical lasers and photosensitizing compounds, including light delivery and dosage parameters, are Photosensitizing Compounds: Their Chemistry, Biology and Clinical Use, published in 1989 by John Wiley and Sons Ltd., Chichester, U.K., ISBN 0 471 92308 7, and Photodynamic Therapy and Biomedical Lasers: Proceedings of the International Conference on Photodynamic Therapy and Medical Laser Applications, Milan, Jun. 24–271992, published by Elsevier Science Publishers B. V., Amsterdam, The Netherlands, ISBN 0 444 81430 2, both of which are incorporated herein by reference.

United States patents related to PDT include U.S. Pat. Nos. 5,095,030 and 5,283,225 to Levy et al.; U.S. Pat. No. 5,314,905 to Pandey et al.; U.S. Pat. No. 5,214,036 to Allison et al; and U.S. Pat. No. 5,258,453 to Kopecek et al., all of which are incorporated herein by reference. The Levy et al. patents disclose the use of photosensitizers affected by a wavelength of between 670–780 nm conjugated to tumor specific antibodies, such as receptor-specific ligands, immunoglobulins or immunospecific portions of immunoglobulins. The Pandey et al. patents are directed to pyropheophorbide compounds for use in standard photodynamic therapy. The Allison et al. patent is similar to the Levy patents in that green porphyrins are conjugated to lipocomplexes to increase the specificity of the porphyrio compounds for the targeted tumor cells. The Kopeck et al. patent also discloses compositions for treating cancerous tissues. These compositions consist of two drugs, an anti-cancer drug and a photoactivatable drug, attached to a copolymeric carrier. The compositions enter targeted cells by pinocytosis. The anti-cancer drug acts after the targeted cell has been invaded. After a period of time, a light source is used to activate the photosensitized substituent.

The potential for combining PDT with immunotherapy was explored by Krobelik, Krosl, Dougherty and Chaplin. See Photodynamic Therapy and Biomedical Lasers, supra, at pp. 518–520. In their study, they investigated a possibility of amplification of an immune reaction to PDT and its direction towards more pervasive destruction of treated tumors. The tumor, a squamous cell carcinoma SCCVII, was grown on female C3H mice. An immunoactivating agent SPG (a high molecular weight B-glucan that stimulates macrophages and lymphoid cells to become much more responsive to stimuli from cytokines and other immune signals) was administered intramuscularly in 7 daily doses either ending one day before PDT or commencing immediately after PDT. Photofrin based PDT was employed; photofrin having been administered intravenously 24 hours before the light treatment. The SPG immunotherapy was shown to enhance the direct killing effect of the PDT. The indirect killing effect (seen as a decrease in survival of tumor cells left in situ) was, however, much more pronounced in tumors of animal not receiving SPG. The difference in the effectiveness of SPG immunotherapy when performed before and after PDT suggested that maximal interaction is achieved when immune activation peaks at the time of the light delivery or immediately thereafter. With SPG starting after PDT (and attaining an optimal immune activation 5–7 days later), it is evidently too late for a beneficial reaction.

Photodynamic therapy (PDT) uses specifically designed drugs such as Foscan.RTM. (Scotia Pharmaceuticals), ALA (DUSA)and Photofin (QLT Phototherapeutics) to destroy rapidly dividing cells. These drugs are selectively retained or generated at rapidly dividing cells and are subsequently excited by light to produce the desired effects. The primary mode of activity usually involves energy transfer from these photoexcited drugs to $O_2$ to produce superoxides or $O_2$ in its singlet state. To date this excitation has been provided by lasers, lamps, and new materials such as laser action in amplifying scattering media. Some of these sources are generally expensive and require complicated delivery systems.

Two of the most important photodynamic therapy drugs are the naturally occurring ALA compound and Photofrin. Both of these are porphyrin compounds that have a peak absorption at 630 nm with a line width of approximately 35 nm. Photofrin has recently received FDA approval for the treatment of esophageal cancer.

U.S. Pat. No. 5,087,636 to Jamieson, et al. discloses a method to identify and destroy malignant cells in mononuclear cell populations. This method includes the steps of contacting a composition of bone marrow cells or other cells with a green porphyrio of a specific compound, irradiating the cell composition with light at a wave length effective to excite fluorescence of the green porphyrio, and then detecting the presence or absence of fluorescence indicating malignancy. This reference also discloses the steps by which the bone marrow cells are removed, separated, washed and diluted to an appropriate concentration for treatment, incubated, centrifuged, and exposed to the irradiating light.

U.S. Pat. Nos. 5,308,608 and 5,149,708 to Dolphin, et al. disclose specific types of porphyrin compounds which may be used for detection, photosensitization, or the destruction of a targeted biological material when the targeted tissue is contacted with the specified porphyrin, and irradiated with light that excites the compound.

U.S. Pat. No. 5,211,938 to Kennedy, et al. discloses a method of detection of malignant and non-malignant lesions by photochemotherapy of protoporphyrin IX precursors. 5-aminolevulinic acid (5-ALA) is administered to the patient in an amount sufficient to induce synthesis of protoporphyrin IX in the lesions, followed by exposure of the treated lesion to a photo activating light in the range of 350–640 nanometers. Naturally occurring protoporphyrin IX is activatable by light which is in the incident red light range (600–700 nanometers) which more easily passes through human tissue as compared to light of other wave lengths which must be used with other types of porphyrins. The use of 5-ALA makes cell fluorescence easier to observe, and also greatly reduces the danger of accidental phototoxic skin reactions in the days following treatment since protoporphyrin IX precursors have a much shorter half life in normal tissues than other popularly used porphyrins.

Another set of prior art references exists which relate to flow cytometry utilizing fluorescence producing compounds. One such prior art reference includes U.S. Pat. No. 5,605,805 to Verwer, et al., which discloses a method for determining the lineage of acute leukemia cells in the sample by fluorocytometry. Other examples of fluorocytometry utilizing fluorescence include U.S. Pat. No. 5,418,169 to Crissman, et al., U.S. Pat. No. 5,556,764 to Sizto, et al., and U.S. Pat. No. 5,627,040 to Bierre.

Present methods relating to cancer screening using fluorescence detection systems require the use of interventional devices such as endoscopes which have the special capability of delivering specified light frequencies to a targeted area within a patient.

Accordingly, the tumor still needs to be sampled by an appropriate biopsy method. Generally, biopsy methods also require some type of sedation or anesthesia. Thus, traditional methods of confirming a malignancy may require at least two interventional surgical procedures.

Thus, there is a need in the art for new and better micro-cannula/endoscope assemblies and methods for using same that can be used to directly visualize the mammary ducts of a breast where visualization is by means of endoscopic devices, direct visualization and offers the additional advantage that the equipment required is comparatively simple to use and is less expensive than the equipment required to create photographic displays from such images. In addition, there is a need in the art for a method of ablating diseased or abnormal tissue which are located during such visualization within the mammary duct.

SUMMARY OF THE INVENTION

The present invention is directed toward the detection and treatment of abnormal growths and cancer located in the mammary ducts of women's breasts which in the present invention is when the cancer is typically between two and three years old with a size of about 0.2 mm. This is over 50 times more sensitive than a standard mammogram. According to the invention, the present invention uses a micro-endoscope having a diameter ranging from 0.5 mm to 1.2 mm to illuminate the targeted part of the body in which cancer is suspected. The light is delivered at a specified wave length to illuminate and treat an area which has previously been subjected to a fluorescent marker or combination of markers which causes atypical or malignant cells to illuminate or fluoresce under observation of light at a specified wavelength. In all cases, introduction of an endoscope into the body requires some type of sedation or general or local anesthesia. However, prior to actual treatment, there must be a confirmed test of cancer.

The present invention provides a fluorescent micro-endoscope apparatus for obtaining a fluorescent image to perform observation and diagnosis and a laser or light source capable of transmitting light in a predetermined wavelength on a diseased portion of a mammary duct.

An object of the present invention is to provide a fluorescent micro-endoscope apparatus which is capable of capturing both normal light image and a fluorescent light image and which has a simple structure.

Another object of the present invention is to provide a fluorescent micro-endoscope assembly which is capable of performing an errorless and accurate diagnosis by correcting the distribution of fluorescent light intensities.

It is another object of the invention to allow physicians to perform a variety of intraductal procedures to display atypical cells with minimal or no discomfort for patients.

It is still another object of the invention to provide convenient, efficient, and economical mammary ductoscopy-breast care.

It is thus an object of the invention to provide a micro-endoscope assembly which can view the interior of a lactiferous duct to ascertain tissue abnormalities and deliver treatment to the tissue at the site.

It is an object of the present invention that it provides a variable energy forms to a tissue site.

It is another object of the present invention to provide a medical instrument of high durability which is easily cleaned and sterilized.

It is also an object of the invention to create a micro-endoscope assembly which can be easily handled by the physician for intraductal treatment.

These and other objects, advantages, and novel features of the present invention will become apparent when considered with the teachings contained in the detailed disclosure which along with the accompanying drawings constitute a part of this specification and illustrate embodiments of the invention which together with the description serve to explain the principles of the invention.

BRIEF DESCRIPTION OF THE DRAWINGS

FIG. 1 is an exploded side elevational view of the endoscope used in the present invention;

FIG. 2 is an enlarged partial cross section of the lens end of the endoscope in FIG. 1;

FIG. 3 is a perspective orientated view of the back end of the endoscope showing a light post and laser post;

FIG. 4 is a perspective view of a portion of the front end of the micro-endoscope assembly;

DETAILED DESCRIPTION OF THE INVENTION

Figure 5:
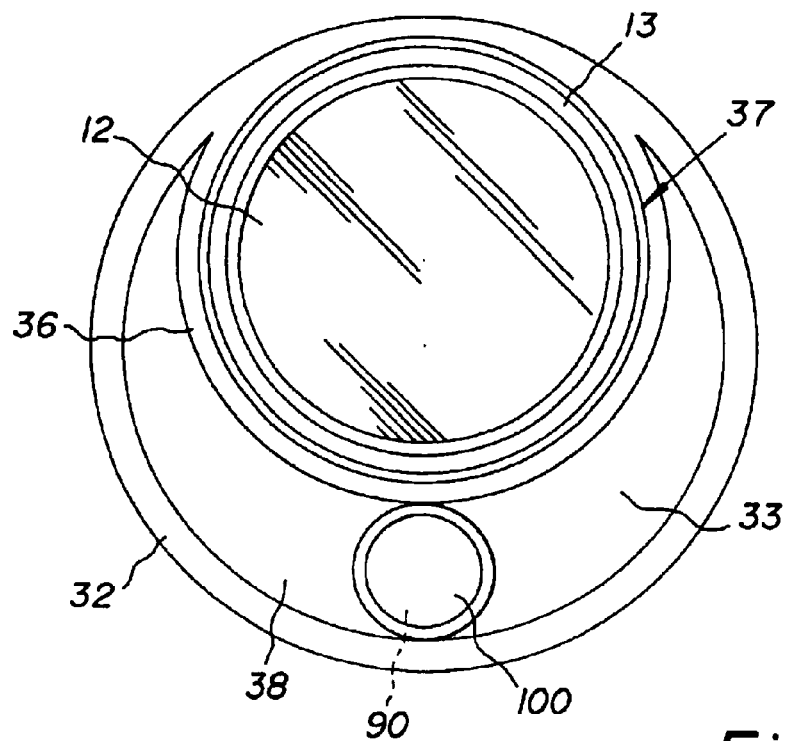
FIG. 5 is an enlarged cross sectional view taken across FIG. 4.

The present invention is directed towards a micro-endoscope assembly 10 which can be used and inserted into the lactiferous ducts of the breast of a woman patient and a method for locating and treating cancer cells in the duct. The lactiferous ducts generally range in number from about six to about twelve in women and lead from areas of the breast to the nipple where they are in parallel vertical orientation with each other. The ducts have a very thin cell wall ranging from 3 to 4 cells in thickness and are resilient. The ducts have a smooth inner surface and white color which resemble visually the interior of a standard PVC pipe.

The best mode and preferred embodiment of the invention is shown in FIGS. 1–5. The micro-endoscope assembly 10 consists of tube or guide cannula 14 which seats and guides the endoscope 12. The cannula 14 has an outer cylindrical wall 16 which defines an internal passageway which runs along its length to seat and guides the endoscope 12. Cannula tube 14 may be a rigid steel tube ranging from 5–20 cm long having an outer diameter ranging from 0.5 mm to approximately 1.2 mm or alternatively may be a semi-rigid tube made of flexible or transparent plastic, or some other suitable material, and having the same or a longer length. The exterior of the cannula is marked with marking indicia 15 as seen in FIG. 4 so that the depth of penetration of the micro-endoscope assembly into the duct can be noted. The marking indicia can be in the form of rings of opaque, translucent or light reacting material or any other suitable geometry which is easily visible to the surgeons eye. The marking indicia can be printed onto the outer surface of the cannula or imbedded in the cannula structure material. Various cannula are envisioned to be interchangeable with the endoscope 12 by unscrewing one guide cannula from the endoscope front hub 18 and its associated connector member 20 and screwing one another on to the connector member.

The endoscope 12 is provided with tube body 17 formed with objective lens 22 at its distal end and image guide 24 as is more clearly shown in FIG. 2. The endoscope 12 has a proximal end in the form of a back member 26 having a light post 27 and a video port 29 as seen in FIG. 3.

The preferred cannula embodiment 30 as seen in FIG. 5 has a cylindrical outer cannula or sheath 32 formed with a beveled distal end 34 as shown in FIG. 4 or a cylindrical end as shown in FIG. 2. The inner wall of sheath 32 defines a cylindrical inner channel 33 which has an inner cylindrical tube 36 eccentrically mounted thereon. The tube 36 defines the endoscope channel 37 and holds endoscope 12. The inner cylindrical tube 36 is eccentrically mounted in cylindrical inner channel 33 to the wall of the cannula sheath 32 and its outer surface together with the inner surface of the sheath or tube 32 to define a moon shaped channel 38 which acts as a channel or passageway providing irrigation and aspiration and is also used as a port through which a fiber optic array or a laser probe 60 can be inserted until for transmission of light energy of predetermined wave length on the patient's duct area containing cells and/or tissue showing abnormal characteristics.

Suitable working devices in the form of laser or light probe 60 can be inserted in the working channel 38 of the micro-endoscope for light wave guides. The generator or energy source is indicated by block diagram 64 and can be used to deliver varied light wave lengths for excitation depending on the fluorescent compound used.

Figure 6:
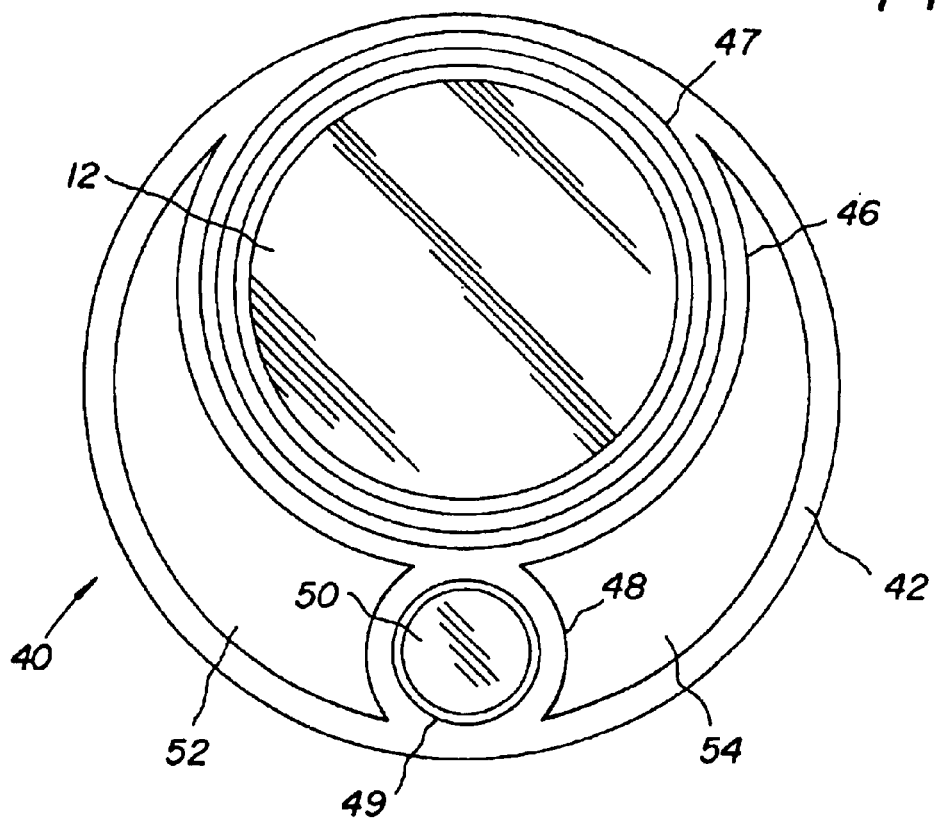
FIG. 6 is an alternate embodiment of the micro-endoscope assembly invention.

A laser fiber or fiber bundle 100 as seen in FIG. 5 and in FIG. 6 can be used to excite the chemically treated tissue within the mammary duct.

In operation, a photosensitive compound is introduced to the cell tissue through the working channel 38. These compounds when administered in appropriate amounts selectively enter into pre-malignant and malignant cells, and provide a "fluorescent marker" in the cells, primarily in the mitochrondia surrounding the nucleus. The compounds which may be used in this method to induce fluorescence include ALA and it's derivatives, 5-ALA, protoporphyrin IX, tetrakis carboxy-phenyl porphine (TCPP), hematoporphyrine derivative, photofrin, and photofrin II and other compounds known in the art to cause fluorescence in pre-malignant or malignant cells. For TCPP, this compound enters live cells via a special transport mechanism found in the outer cellular wall. TCPP will not enter dead cells, thus making it a good compound for in viro application. The above compounds will cause pre-malignant or malignant cells to fluoresce when exposed to frequencies of light which match the excitation frequency of the particular compound used; however healthy cells will generally not fluoresce.

Other possible compounds which may be used include uroporphyrin; coproporphyren; tetraphenylporphine-sulfonate (TPPS); and tetraporphen (4, N-methyulpyridil) (TMPP). These compounds, when administered in appropriate amounts, selectively enter pre-malignant and malignant cells, and provide a fluorescent marker inside the cell, primarily in the mitochrondia surrounding the nucleus. The compounds can be supplied singularly or in combination to provide maximum effectiveness.

After introduction of predetermined dosage of the chemical compound(s) to the mammary ducts, the compound incubates for a period of time ranging between 1 and 4 hours to allow the pre-malignant and malignant cells to interact with the compounds. The average time for interaction time for TCPP is 1–2 hours. Other compounds may take longer and the absorption time is set out in the prior art.

The micro-endoscope is inserted into the mammary duct and the light source 64 is tuned to provide light which matches the excitation frequency and the treatment frequency. One such light source for photofrin and similar photodynamic therapy drugs is a pulsed (150 nanosecond pulse width) Nd:YAG laser that outputs to a frequency doubler such as a KTP crystal which is used to drive a dye laser in a number of wave lengths. For TCPP, the excitation frequency ranges from 380–400 nm and for endogenous protoporphyrin IX the absorbtion ranges is 412 nm. For other compounds which absorb blue light, the wave length ranges from 300 nm to 450 nm. Compounds which absorb red spectrum light are difficult to channel through small endoscopes unless expensive lasers are used. The surgeon observing the cells looks for cells which fluoresce in the visible red range (approximately 630 nanometers) generated by light source 65. If desired, a single source 64 can be used to generate light a specific different wavelengths. When the fluorescence is observed, the light wavelength is changed to the excitation range of the compound and directed at the fluorescent tissue for a series of exposures ranging from 1 to 10 in number and 5 to 10 minutes in length. This exposure causes the formation of $O_2$ in the atypical cells forming a toxin which kills the cells. If desired, antiseptic or a flushing solution such as saline can be applied to the duct interior and the contents withdrawn via the micro-endoscope. After treatment, the micro-endoscope is withdrawn from the mammary duct. Alternatively, the flushing step can be performed after withdrawal of the micro-endoscope from the mammary duct.

An alternate embodiment of the cannula 40 is shown in cross section in FIG. 6. This embodiment has a cylindrical outer cannula or sheath 42 which defines a cylindrical inner channel 43 in which an inner cylindrical tube 46 is eccentrically mounted to the wall of sheath 42. The cylindrical tube 46 defines the endoscope channel conduit 47 to hold the endoscope 12. A second smaller cylindrical tube 48 is eccentrically mounted in channel 43 adjacent to and integral with a portion of the wall of tube 46 and a wall of the cannula 42 to form a laser or light probe channel 49 which holds the laser or light probe 60. The cylindrical tube structure 46 divides the moon shaped channel up into two separated segments 52 and 54 which can also serve as the irrigation and aspiration channels for the assembly.

FIG. 1 also shows the endoscope 12 with the lens tube 17 and tube portion 19 coupled between hub 18 and back end 26. Tube 19 includes a passageway in it's interior capable of holding fiber optic strands and/or illumination strands. Such strands run from video port 29, through tube portion 19 into hub 18. The strands run through hub 18 into the inner passageway of tube portion 17 though or outside of the working channel, as described in more detail below. These strands provide both a light source of desired wavelength or multiple wavelengths to the area of interest and a video source to the video port, allowing the physician to see a fluoresced image of the area of the duct in which treatment is being undertaken. The back end 26 is formed with a light source post connector 27. The tube portion 14 which has an outer diameter of approximately 1.2 mm has a working channel, a plurality of light fibers and a lens 22. The light fibers 22 run the length of the guide tube 17 and provide light to the areas of interest. The light fibers are commercially available. The tube cannula 14 can alternately carry the light fibers or have them molded in the tube material. The lens 22 also runs longitudinally down inner passage of guide tube 17.

The endoscope 12 is used in conjunction with a video monitor and prismatic screen (not shown). The video port 29 is coupled to a video camera which is in turn coupled to a video monitor as is well known in the art and has an attached prismatic screen manufactured by Acueity Inc. The video camera may be of many different commercially available models, although CCD cameras are particularly useful in this type of application. Specifically, a Panasonic GS99-NTSC medical video endoscopycamera, from Matsushita Electric Corporation of America, has been found to be useful. Moreover, it has been found that in such a camera ¼ inch CCD chip is more advantageous than a ½ inch CCD chip, because it provides an image with smaller pixels. Such chips are included in CCD cameras and also are commercially available from many sources such as, for example, the Sony Corporation of America. The video monitor may be any of a number of commercially available video monitors.

The principles, embodiments and modes of operation of the present invention have been described in the foregoing specification. The invention that is sought to be protected herein, however, is not to be considered as limited to the particular forms disclosed, since these are to be regarded as illustrative rather than restrictive.

What I claim is:

1. A method of treating atypical tissue in the mammary duct of a woman's breast using a micro-endoscope assembly having a distal end with a diameter ranging from 0.5 mm to about 1.2 nm, the method comprising the steps of:
    a. administering a dosage of a chemical fluorescent marker compound into the interior of a mammary duct;
    b. incubating said fluorescent marker compound in the duct from about 1 to about 4 hours;
    c. inserting the distal end of the micro-endoscope into the mammary duct of a woman patient;
    d. transmitting light into the dosed mammary duct to match the excitation frequency of the marker compound causing atypica tissue to fluoresce;
    e. viewing the interior of the duct until the location of tissue fluorescence is ascertained;
    f. positioning the micro-endoscope assembly proximate the atypical tissue;
    g. transmitting light through said micro-endoscope onto the atypical tissue at a wave length suitable to cause fluoresced cells to be destroyed; and
    h. withdrawing the micro-endoscope from said mammary duct.

2. A method as claimed in claim 1 wherein said transmitted light to match the excitation frequency of the marker compound is light having a wave length ranging from about 350 nm to about 450 nm.

3. A method as claimed in claim 1 wherein said transmitted light in steps (d) and (g) have a wave length ranging from about 350 nm to about 700 nm.

4. A method as claimed in claim 1 wherein said fluorescent marker compound is selected from a group consisting of aminolevulinic acid (ALA) and its derivatives, 5-aminolevulinic acid (5-ALA), protoporphyrin IX, tetrakis carboxy-phenyl porphine (TCPP), hematoporphyrine derivative, photofrin, and photofrin II.

5. A method as claimed in claim 1 wherein said fluorescent marker compound is selected from a group consisting of uroporphyrin; coproporphyren; tetraphenylporphine-sulfonate (TPPS); and tetraporphen (4, N-methyulpyridil) (TMPP).

6. A method of treating atypical tissue in the mammary duct of a woman's breast using a micro-endoscope assembly having a distal end with a diameter ranging from 0.5 mm to about 1.2 mm, the method comprising the steps of:
    a. administering a dosage of a chemical fluorescent marker compound into the interior of a mammary duct;
    b. incubating said fluorescent marker compound in the duct from about 1 to about 4 hours
    c. inserting the distal end of the micro-endoscope into the mammary duct of a woman patient;
    d. transmitting light into the dosed mammary duct at a specific wave length to match the excitation frequency of the marker compound causing atypical cells to fluoresce at a longer wavelength than the excitation frequency;
    e. viewing the interior of the duct to ascertain tissue fluorescence location;
    f. positioning the micro-endoscope assembly for direction of light of the atypical tissue;
    g. transmitting light through said micro-endoscope onto the atypical tissue at a designated wave length for a period of time suitable to generate cytotoxic singlet oxygen in the fluoresced cells causing same to be necrosed; and
    h. withdrawing the micro-endoscope from said mammary duct.

7. A method as claimed in claim 6 wherein said transmitted light to match the excitation frequency of the marker compound is light having a wave length ranging from about 350 nm to about 450 nm.

8. A method as claimed in claim 6 wherein said transmitted light in step (g) has a wave length ranging from about 600 nm to about 700 nm.

9. A method as claimed in claim 6 wherein said fluorescent marker compound is selected from a group consisting of 5-aminolevulinic acid (5-ALA), protoporphyrin IX, tetrakis carboxy-phenyl porphine (TCPP), hematoporphyrine derivative, photofin, and photofrin II.

10. A method as claimed in claim 6 wherein said fluorescent marker compound is selected from a group consisting of uroporphyrin; coproporphyren; teteaphenylporphine-sulfonate (TPPS); and tetraporphen (4, N-methyulpyridil) (TMPP).

11. A method of treating atypical tissue in the mammary duct of a woman's breast using a micro-endoscope assembly having a distal end with a diameter ranging from 0.5 mm to about 1.2 mm, the method comprising the steps of:
    a. administering a dosage of a chemical fluorescent marker compound into the interior of a mammary duct by injecting the compound in the duct;
    b. incubating the dosage in the duct for a period of about 1 to about 4 hours to allow atypical cells to interact with the marker compound and absorb the marker compound in the mitochrondia surrounding the cell nucleus.

c. inserting the distal end of the micro-endoscope into the mammary duct of a woman patient;

d. transmitting light through the micro-endoscope into the dosed mammary duct to match the excitation frequency of the marker compound causing atypical cells to fluoresce;

e. viewing the interior of the duct until the location of tissue fluorescence is ascertained;

f. positioning the micro-endoscope proximate the abnormal tissue at a distance to receive light transmitted through the micro-endoscope;

g. transmitting light through said micro-endoscope onto the atypical tissue at a wave length ranging from about 600 nm to about 700 nm for a period of time suitable to cause fluoresced atypical cells to be destroyed; and h. withdrawing the micro-endoscope from said mammary duct.

12. A method as claimed in claim 11 including the additional step after atypical cell destruction of lavaging the interior of the mammary duct.

13. A method as claimed in claim 11 wherein said marker compound consists of a group consisting of ALA and photofrin.

14. A method as claimed in claim 11 wherein said transmitted light in steps (d) and (f) have a wave length ranging from about 350 nm to about 700 nm.

15. A method as claimed in claim 11 wherein said fluorescent marker compound is selected from a group consisting of 5-aminolevulinic acid (5-ALA), protoporphyrin IX, tetrakis carboxy-phenyl porphine (TCPP), hematoporphyrine derivative, photofrin, and photofrin II.

16. A method as claimed in claim 11 wherein said fluorescent marker compound is selected from a group consisting of uroporphyrin; coproporphyren; tetraphenylporphinesulfonate (TPPS); and tetraporphen (4, N-methyulpyridil) (TMPP).

17. A method as claimed in claim 11 wherein said transmittal light causing said atypical cells to fluoresce ranges from about 350 nm to about 400 nm.

18. A method of treating diseased tissue in the mammary ducts of a patients breast with a micro-endoscopic assembly and a cannula sheath having a diameter ranging from about 0.5 mm to about 1.2 mm wherein said endoscope assembly includes a guide having a working channel, a light source and a lens; said guide forming an irrigation channel and an energy transmitting probe moveably mounted in said endoscope; said method comprising the steps of:

a. inserting the distal end of said cannula sheath into a mammary duct of a dilated nipple of a breast which has been treated with a fluorescent producing compound said fluorescent producing compound is being incubated in said duct from about 1 to about 4 hours.

b. inserting a micro-endoscope into said cannula sheath and transmitting a light source causing atypical cells to fluoresce;

c. projecting an image of the interior of said breast duct on a video monitor;

d. moving said micro-endoscope along said duct until an area of atypical cells is detected by viewing cells which fluoresce;

e. positioning said micro-endoscope in said duct;

f. applying light at a specific wavelength to said probe to said atypical cell area for a period of time sufficient to cause atypical cell destruction;

g. irrigating the interior of said breast duct by injecting liquid through an irrigation channel of said micro-endoscope; and h. extracting destroyed tissue from said breast duct.

19. A method as claimed in claim 18 wherein said transmitted light in steps (b) and (f) have a wave length ranging from about 350 nm to about 700 nm.

20. A method as claimed in claim 18 wherein said fluorescent producing compound is selected from a group consisting of aminolevulinic acid (ALA) and its derivatives, 5-aminolevulinic acid (5-ALA), protoporphyrin IX, tetrakis carboxy-phenyl porphine (TCPP), hematoporphyrine derivative, photofrin, and photofrin II.

21. A method as claimed in claim 18 wherein said fluorescent producing compound is selected from a group consisting of uroporphyrin; coproporphyren; tetraphenylporphinesulfonate (TPPS); and tetraporphen (4, N-methyulpyridil) (TMPP).

* * * * *